(12) United States Patent
Masuda et al.

(10) Patent No.: US 7,357,805 B2
(45) Date of Patent: Apr. 15, 2008

(54) CLIP DEVICE FOR ENDOSCOPE AND CLIP FOR ENDOSCOPE FOR USE THEREIN

(75) Inventors: Haruhiko Masuda, Akita (JP); Shinetsu Harada, Akita (JP)

(73) Assignee: Sumitomo Bakelite Company, Tokyo (JP)

(*) Notice: Subject to any disclaimer, the term of this patent is extended or adjusted under 35 U.S.C. 154(b) by 266 days.

(21) Appl. No.: 10/498,162

(22) PCT Filed: Dec. 12, 2002

(86) PCT No.: PCT/JP02/13032

§ 371 (c)(1),
(2), (4) Date: Jun. 9, 2004

(87) PCT Pub. No.: WO03/053256

PCT Pub. Date: Jul. 3, 2003

(65) Prior Publication Data

US 2005/0049618 A1    Mar. 3, 2005

(30) Foreign Application Priority Data

Dec. 13, 2001  (JP) ............................. 2001-379431
Feb. 14, 2002  (JP) ............................. 2002-036107
Oct. 4, 2002   (JP) ............................. 2002-292847
Oct. 4, 2002   (JP) ............................. 2002-292848

(51) Int. Cl.
*A61B 17/10* (2006.01)

(52) U.S. Cl. .................. 606/142; 606/139; 606/151

(58) Field of Classification Search ............ 606/151, 606/142, 143, 139; 29/243.56
See application file for complete search history.

(56) References Cited

U.S. PATENT DOCUMENTS

| | | | | | |
|---|---|---|---|---|---|
| 5,156,609 A | * | 10/1992 | Nakao et al. | ............... | 606/142 |
| 5,171,247 A | * | 12/1992 | Hughett et al. | ............. | 606/142 |
| 5,174,276 A | * | 12/1992 | Crockard | ................... | 600/104 |
| 5,222,961 A | * | 6/1993 | Nakao et al. | ............... | 606/143 |
| 5,368,600 A | | 11/1994 | Faille et al. | | |
| 6,494,886 B1 | * | 12/2002 | Wilk et al. | ................. | 606/142 |

FOREIGN PATENT DOCUMENTS

| | | | |
|---|---|---|---|
| JP | 53-20957 | * | 6/1978 |
| JP | 61-015852 | | 5/1986 |
| JP | 63-6016 | * | 2/1988 |
| JP | 09-192137 | | 1/1997 |
| WO | WO 91/09569 | | 7/1991 |
| WO | WO 97/13466 | | 4/1997 |

* cited by examiner

*Primary Examiner*—Michael J. Hayes
*Assistant Examiner*—Michael G. Mendoza
(74) *Attorney, Agent, or Firm*—Smith, Gambrell & Russell

(57) ABSTRACT

A clipping device improves defects that the clip can not be again opened once the clip is closed, and that it is necessary to execute the operation in a state in which the clip is not sufficiently opened. The invention provides a clip device for an endoscope constituted by a clipping means having a pair of arm portions which are allowed to be opened and closed, an operating means for holding the arm portions of the clipping means so as to open and close the arm portions, a fixing means for fixing the arm portions after closing the arm portions, and an arranging means for arranging the fixing means in an outer side of the arm portion.

6 Claims, 11 Drawing Sheets

FIG.13
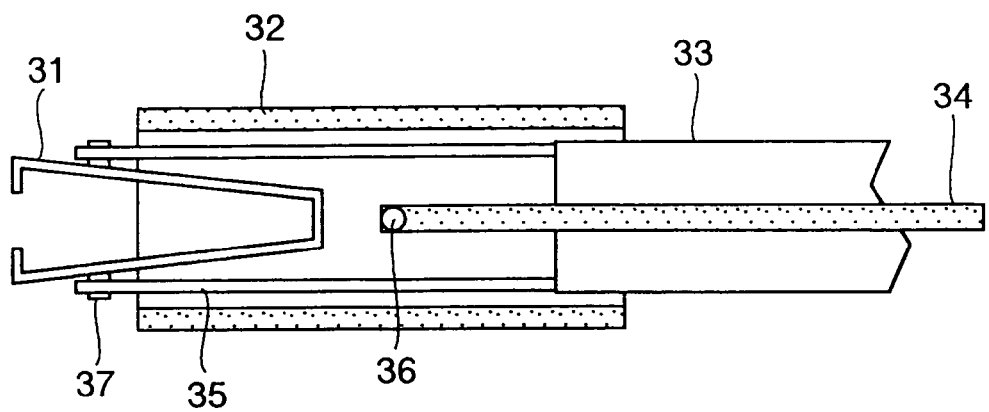
(a)
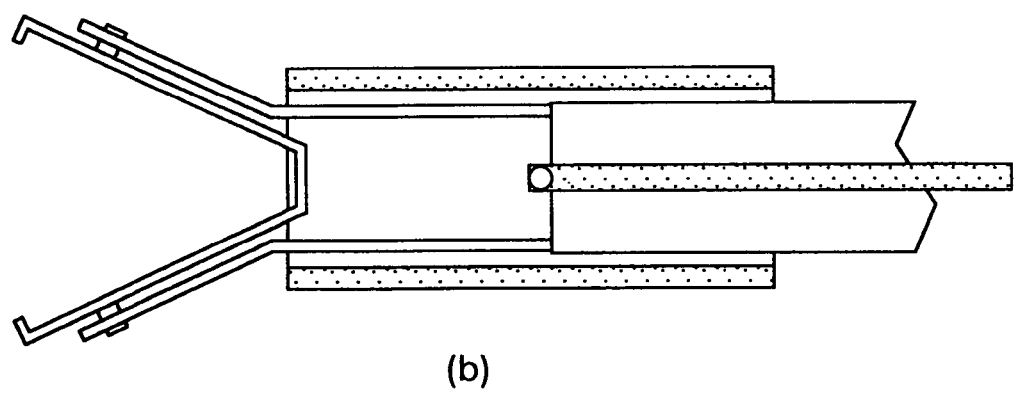
(b)

CLIP DEVICE FOR ENDOSCOPE AND CLIP FOR ENDOSCOPE FOR USE THEREIN

TECHNICAL FIELD

The present invention relates to a clip device for an endoscope. The present invention relates to a clip device used for a marking or the like for clarifying an area to which a ligature or resection treatment is applied in a bleeding portion in a biological tissue, for example, under an endoscopic treatment, and a clip used for the clip device.

PRIOR ART

A method of ligating the bleeding portion by introducing a clip in an endoscopic manner is much applied to the bleeding within a body cavity, however, such a clip is disclosed, for example, in JP-U-53-20957. This invention is constituted by a clip in which a pair of clamping pieces are connected in a rear end and are crossed to each other in an intermediate portion and an inclined surface is formed in each of front and rear outer surfaces of the crossing portion, and a fastening device which is slid on the inclined surface of the clip so as to open and close the clip, and an introduction device for sliding the fastening device.

In this structure, the opening and closing of a pair of clamping pieces are open to the maximum so as to be in a state capable of gripping the tissue, at a time when the fastening device slides between the rear end of the clip and the crossing portion, and next, at a time of pressing a pair of clamping pieces against the tissue to be clipped so as to slide the fastening device to a front side of the crossing portion, a pair of clamping pieces are closed so as to clip the tissue.

However, since this structure can only press out the fastening device to the front side, there is a defect that the clip can not be opened once the clip is closed. Further, in order to make the clip to open to the maximum, it is necessary to stop the fastening device just before the crossing portion of the clip, however, it is hard to adjust and position the fastening device due to a sliding resistance of the fastening device, so that there is a case that the fastening device passes a point where the clip is opened to the maximum, and it is necessary to execute the operation under a state in which the clip is not sufficiently opened.

Further, the clip device moves into the fastening device to which the crossing portion of the clip is fixed, by catching the rear end of the clip by a hook having a release cord and pulling the release cord, and a pair of clamping pieces are opened to the maximum so as to be in a state capable of gripping the tissue. Next, the clip further moves within the fastening device by pressing a pair of clamping pieces against the tissue to be clipped and again pulling the release cord, and a pair of clamping pieces are closed so as to clip the tissue.

However, since the clip device executes the opening and closing operation on the basis of a series of operations of pulling the release cord, the clip can not be returned to the state before entering into the crossing portion in the case that the crossing portion of the clip once enters into the fastening device. In other words, the clip device has a defect in that once the clip is closed, it can not be again opened. Further, in order to open the clip to the maximum, it is necessary to stop the fastening device just before the crossing portion of the clip, however, it is impossible to adjust the position due to the sliding resistance of the fastening device, and the fastening device passes the point where the clip is opened to the maximum, so that there is a case that it is necessary to execute the operation in a state in which the clip is not sufficiently opened.

Further, in JP-B2-63-6016, there is disclosed a method of mounting the clip to the clip device. Since the clip is fixed in a state in which a base end portion of the clip is engaged with a hook provided in the clip device, it is necessary to execute a complicated operation of applying the clip to the hook while gripping the clip by one hand at a time of mounting, so that an operator who is not accustomed to this operation requires a lot of time for this operation.

DISCLOSURE OF THE INVENTION

An object of the present invention is to provide a clipping device which improves defects that the clip can not be again opened once the clip is closed, and that it is necessary to execute the operation in a state in which the clip is not sufficiently opened.

Further, another object of the present invention is to provide a method of easily mounting the clip so as to shorten a mounting time.

In other words, in accordance with the present invention, there is provided a clip device for an endoscope comprising:

a clip having a pair of arm portions which are allowed to be opened and closed;

an operating means for holding the arm portions of the clipping means so as to open and close the arm portions;

a fixing means for fixing the arm portions in a closed state after closing the arm portions; and an arranging means for arranging the fixing means in an outer side of the arm portion.

In the clip device for the endoscope mentioned above, it is preferable that the arm portions of the clip are connected in a base portion in a state in which a width thereof is continuously reduced around a part or an entire of the arm portions.

In the clip device for the endoscope mentioned above, it is preferable that the fixing means and the clip are previously arranged in a small hole provided on a plate, and are thereafter loaded to the device.

Further, in accordance with the present invention, there is provided a clip for an endoscope, the clip being used for a clipping device for the endoscope, wherein a mechanism for fixing to the clipping device for the endoscope is provided in arm portions of the clip.

Further, in accordance with the present invention, there is provided a clipping device for an endoscope having the clip for the endoscope mentioned above.

Further, in accordance with the present invention, there is provided a clipping device for an endoscope comprising:

a hollow member having at least a pair of operating means in a leading end, the operating means being constituted by an elastic operating arm;

an outer member covering the hollow member;

a control member connected to the outer member;

a clip; and a fixing means for fixing the clip after clipping, wherein the clip has a means for fixing to the operating arm, and the operating means are opened and closed by moving the control member connected to the outer member in an axial direction.

Further, in accordance with the present invention, there is provided a clipping device for an endoscope comprising:

a hollow member having at least a pair of operating means in a leading end, the operating means being constituted by an elastic operating arm;

an outer member covering the hollow member;
a control member connected to the outer member;
a clip; and
a fixing means for fixing the clip after clipping,
wherein the operating arms have a means for fixing to the clip, and the operating means are opened and closed by moving the control member connected to the outer member in an axial direction.

BRIEF DESCRIPTION OF THE DRAWINGS

FIGS. 1(a) and 1(b) are views showing an outline of a clipping device corresponding to an embodiment in accordance with the present invention, in which FIG. 1(a) is a general view and FIG. 1(b) is an enlarged view of a connection portion between a clip and an operating means;

FIGS. 3(a) and 3(b) are views for describing another embodiment of the operating means of the clipping device in accordance with the present invention, in which FIG. 3(a) is a view showing a state in which the clip is closed, and FIG. 3(b) is a view showing a state in which the clip is opened;

FIGS. 13(a) and 13(b) are cross sectional views showing a state in which the clip for the endoscope in accordance with the present invention is mounted to the clipping device, in which FIG. 13(a) is a view showing a state in which the clip for the endoscope is closed, and FIG. 13(b) is a view showing a state in which the clip for the endoscope is opened.

BEST MODE FOR CARRYING OUT THE INVENTION

Figure 4:
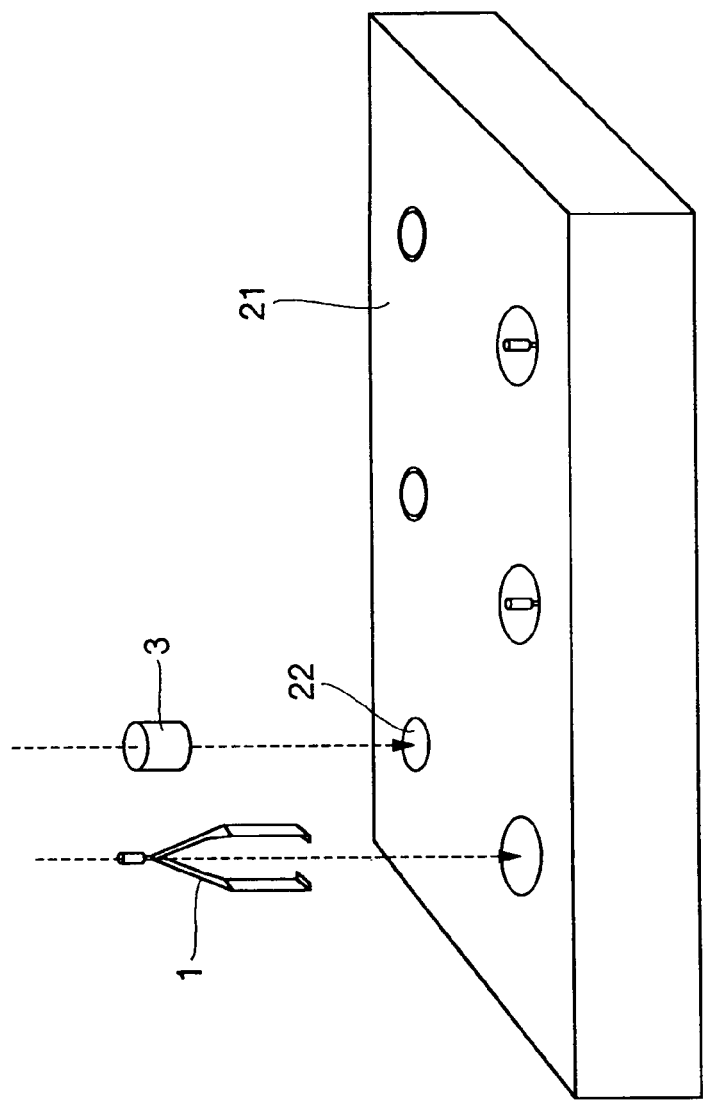
FIG. 4 is a view showing a state in which the clip and the fixing means are set to a plate.
Figure 5:
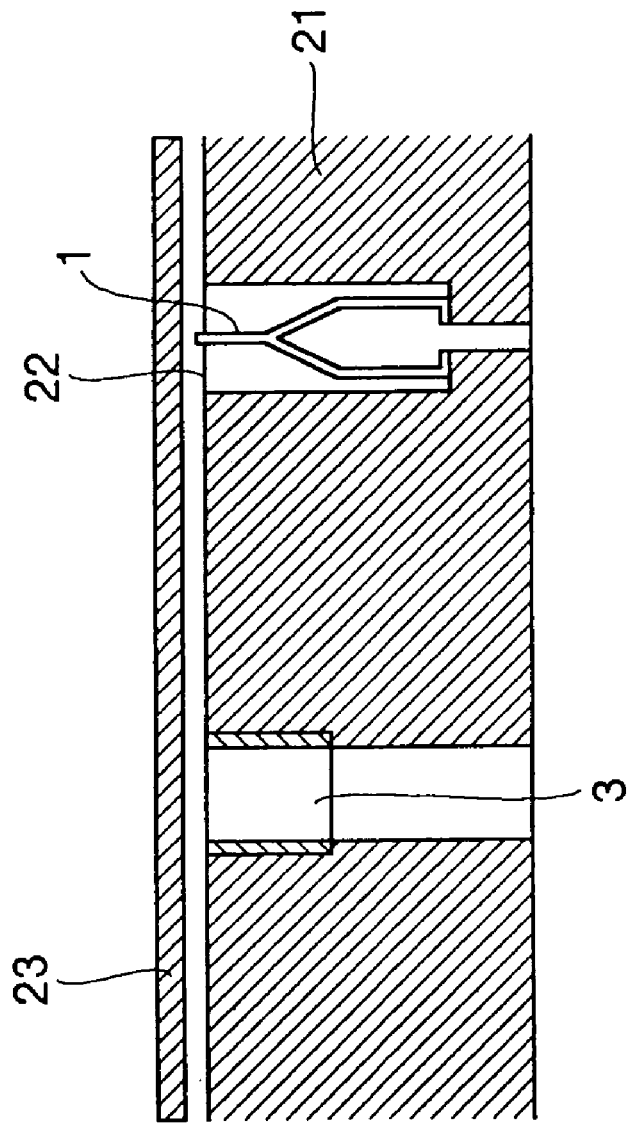
FIG. 5 is a view showing a cross section of the plate at a time when the clip and the fixing means are set to the plate.
Figure 7:
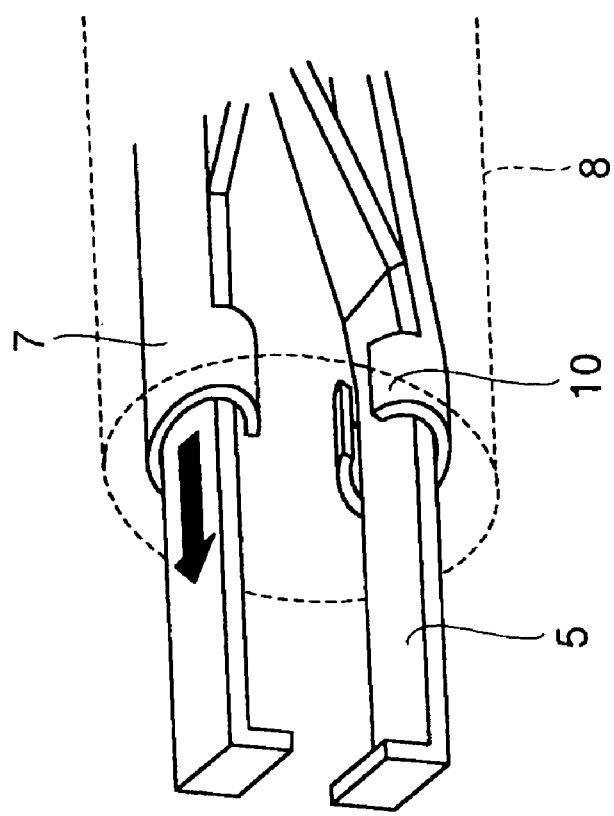
FIG. 7 is a view showing a state in which the clip is loaded.
Figure 8:
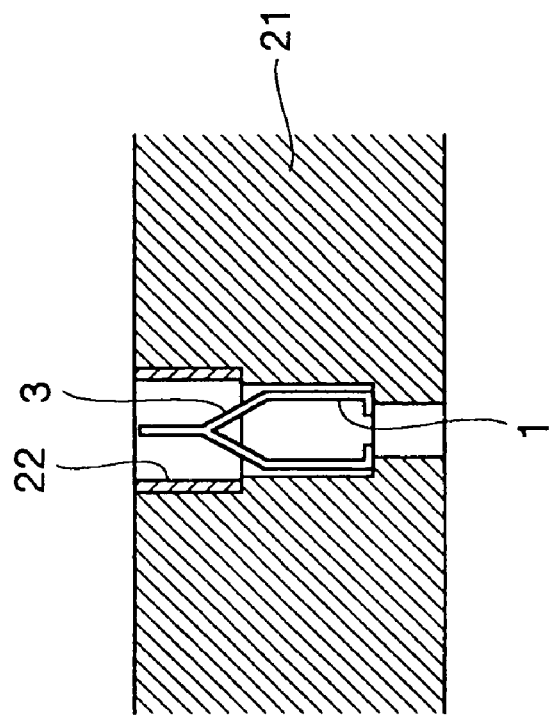
FIG. 8 is a view for describing a method for loading the fixing means and the clip by one operation.

A description will be in detail given below of the present invention by using embodiments. FIGS. 1(a) and 1(b) are views showing a clipping device for an endoscope corresponding to an embodiment in accordance with the present invention, in which FIG. 1(a) is a general view and FIG. 1(b) is an enlarged view of a connection portion between a clip and an operating means. FIG. 2 is a view showing an embodiment of the clip, and FIGS. 3(a) and 3(b) are views showing another embodiment of the operating means in accordance with the present invention, in which FIG. 3(a) shows a state in which the clip is closed, and FIG. 3(b) shows a state in which the clip is opened. FIG. 4 is a view showing a state in which the clip and the fixing means are set to a plate. FIG. 5 is a cross sectional view of the plate at a time when the clip and the fixing means are set to the plate, and FIGS. 6(a) to 6(d) are views for describing a method of mounting a clip to a clip device for an endoscope in accordance with the present invention. FIG. 7 is a view showing a state in which the clip is loaded, FIG. 8 is a view for describing a method for loading the fixing means and the clip by one operation, FIGS. 9(a) to 9(e) are views for describing a method of using the clipping device for the endoscope in accordance with the present invention.

Figure 1:
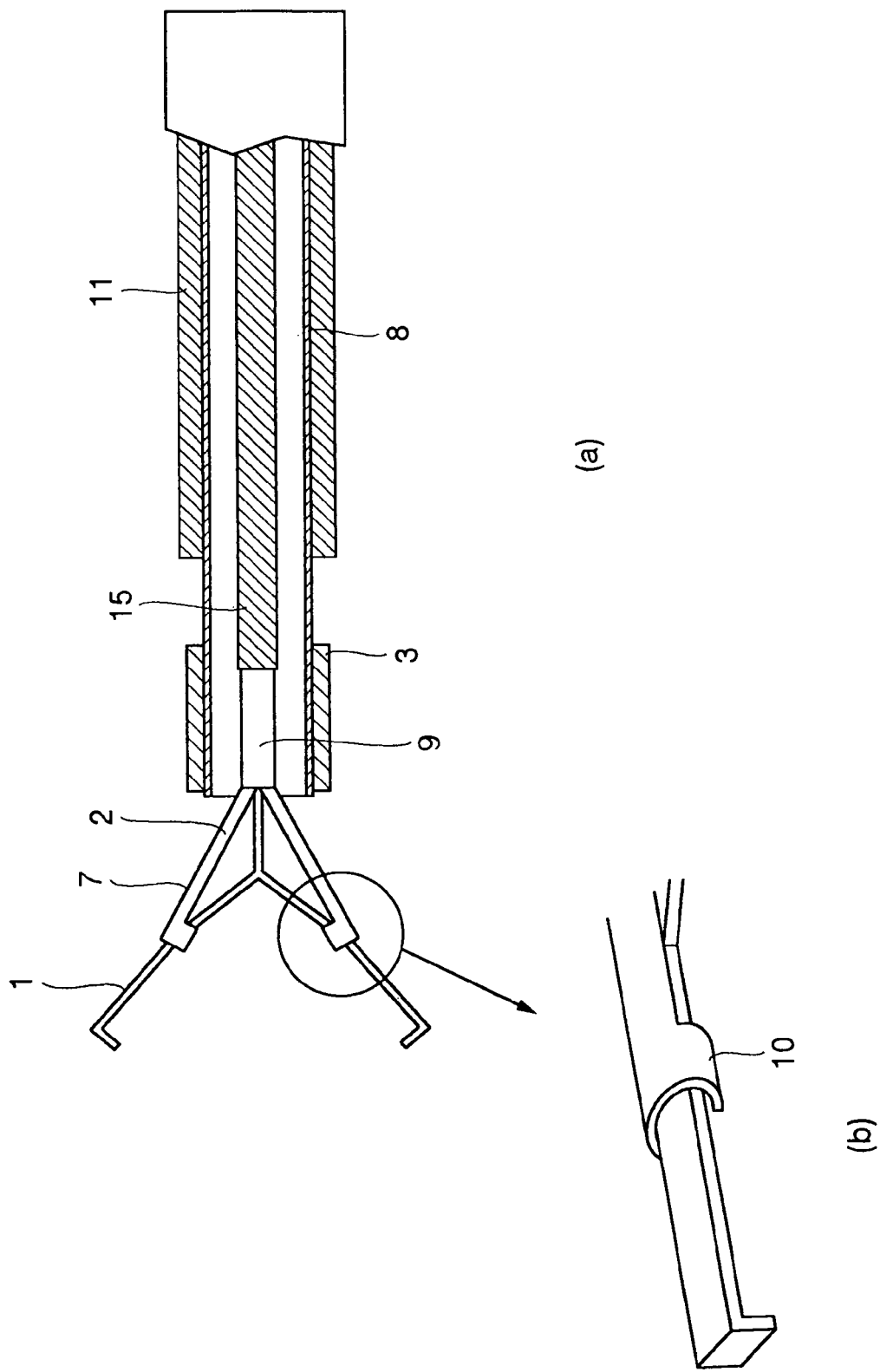
Figure 2:
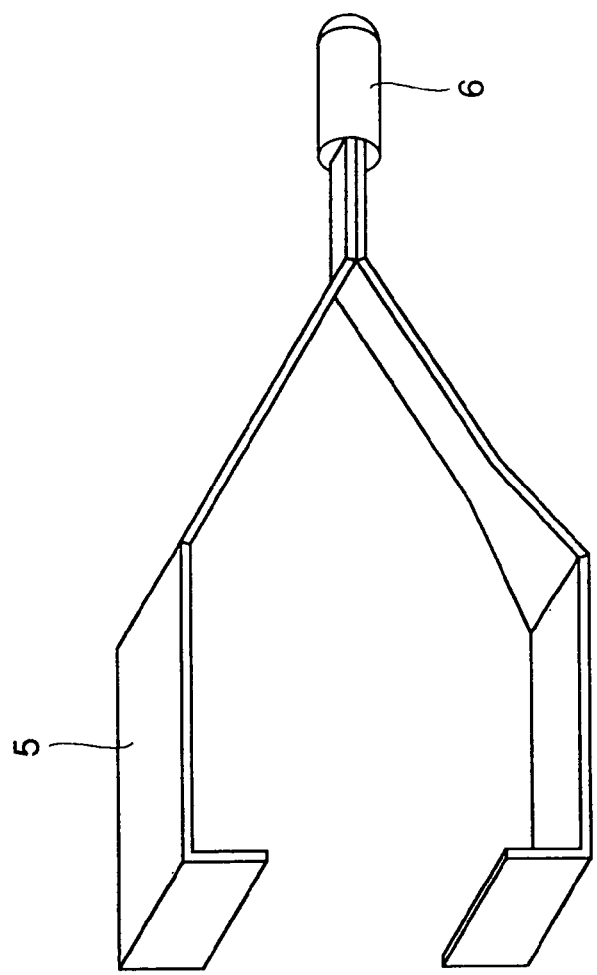
FIG. 2 is a view for describing the clip in accordance with the present invention.

The clipping device in FIG. 1 is constituted by a clip 1, an operating means 2, a fixing means 3 and a pushing tube 11 for sliding the fixing means 3 to a front side.

The clip 1 is formed, for example, by a sheet metal as shown in FIG. 2, and has a pair of arm portions 5, and the arm portions 5 are connected in a rear end connection portion 6. The connection portion 6 is preferably structured as a hinge structure, however, may be structured by simply bonding the arm portions to each other by means of a welding or the like, or folding one sheet metal plate in an illustrated shape. A leading end of the arm portion 5 is folded inside at a fixed angle so as to eat into a tissue.

Further, in order to fit the arm portions 5 to a hook 10 provided in an operating arm 7 mentioned below, the structure is made such that the width of the connection portion 6 is smaller than the width of the arm portion 5 at its widest part, and the width is continuously reduced from the arm portion 5 toward the connection portion 6 along a part of or along the entire length of the arm portion 5.

The operating means 2 is constituted by a combination of a pair of operating arms 7 and a sheath 8 as shown in FIG. 1. A wire 15 for executing an opening and closing operation of the operating arms 7 is connected to a rear end of the operating arms 7, and executes the opening and closing operation of the operating arms 7 in a remote manner.

The operating arms 7 can employ a structure formed by bonding rear ends of two C-shaped leaf springs. This structure is always in an open state, however, the operating arms 7 are elastically deformed so as to be in a closed state in the case that the operating arms 7 are received in an inner cavity of the sheath 8, and the state in which the operating arms 7 are open is restored on the basis of a spring stress of the operating arms 7 in the case that the operating arms 7 are slid so as to come out from the sheath 8.

Figure 3:
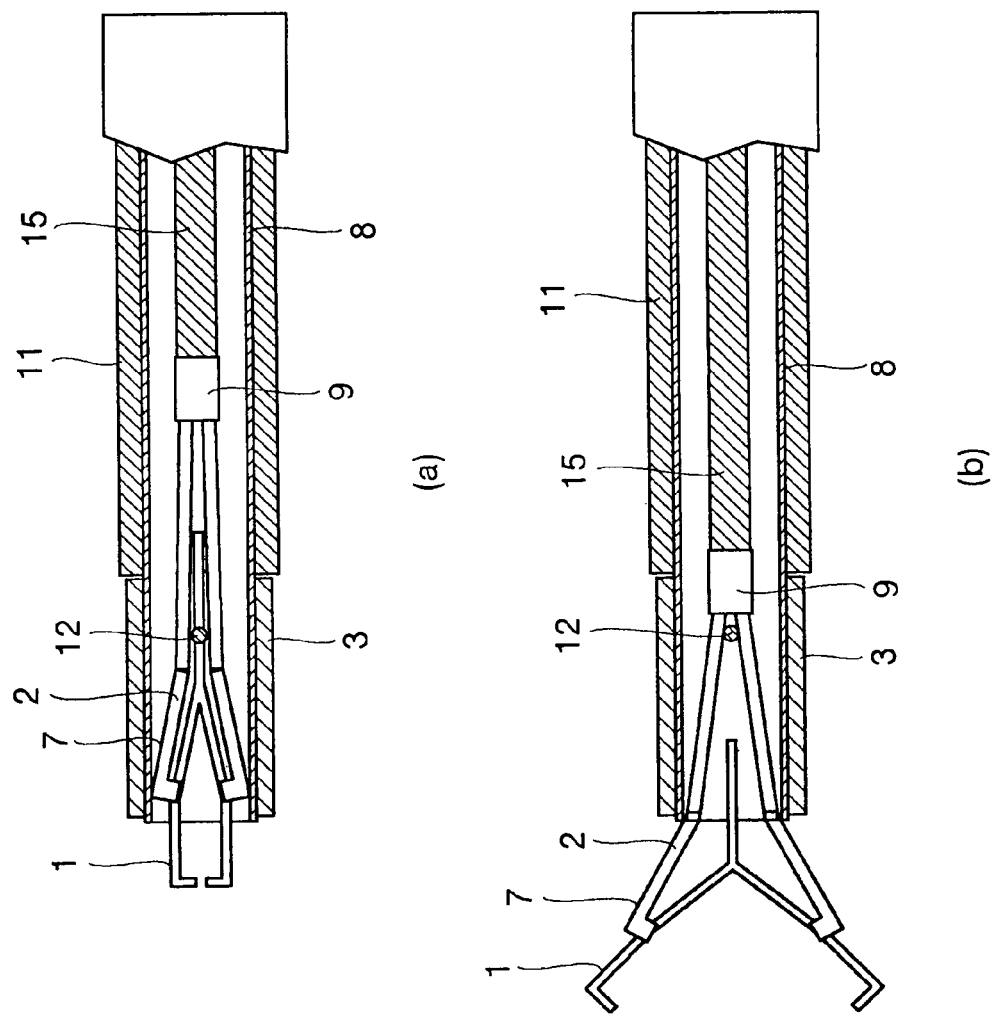

The means for opening and closing the operating arm 7 is not limited to this, and may employ, for example, another embodiment as shown in FIG. 3. In this embodiment, a pair of operating arms 8 connected in the rear ends are arranged within the sheath 8 with holding a rod 12 provided in a diametrical direction of the inner cavity of the sheath 8 therebetween. When sliding the operating arms 7 to a front side so as to move the connection portions of the operating arms 7 close to the rod 12, the operating arms 7 are opened (a state shown in FIG. 3(b)), and when they are moved backward, the operating arms 7 are closed (a state shown in FIG. 3(a)). Two embodiments are exemplified, however, the present invention is not limited to them in the embodiment of the operating means 2.

The hook 10 is provided in a leading end of the operating arm 7, and has a structure that the hook 10 can fix the arm portions 5 in a detachable state by inserting the arm portions 5 of the clip 1 to an inner portion of the hook 10. Further, the connection portion 6 of the clip 1 is inserted to a base portion 9 of the operating arm, and is fixed in a detachable state. In other words, the clip 1 is fixed to the operating means 2 at three points comprising a pair of operating arms 7 of the operating means 2 and the base portion 9, and opens and closes the arm portion 5 of the clip 1 by taking the operating means 2 in and out from the sheath 8.

The fixing means 3 is arranged on an outer periphery of the leading end portion of the sheath 8, and executes an extrusion by sliding a pushing tube 11 provided in an outer side of the sheath 8 to a front side. The clip 1 is fixed in a closed state by gripping the tissue by means of the arm portions 5 of the clip 1 and thereafter sliding the fixing means 3 to a front side so as to arrange in the arm portion 5 of the clip 1.

Next, a description will be given of a loading of the fixing means and the clip.

As shown in FIGS. 4 and 5, the clip 1 and the fixing means 3 are previously set to a small hole 22 provided in a plate 21. A step is provided in the small hole, and the clip 1 and the fixing means 3 are held in a state of striking against the step. In the case of carrying the plate, an upper surface of the plate 21 is covered by the plate cover 23, thereby preventing the clip 1 and the fixing means 3 from falling away from the plate 21.

In this case, a description will be briefly given of a mounting method of the clip 1 in accordance with the present invention by using FIGS. 6(a) to 6(d), and an effect of the present invention is more clarified.

Figure 6:
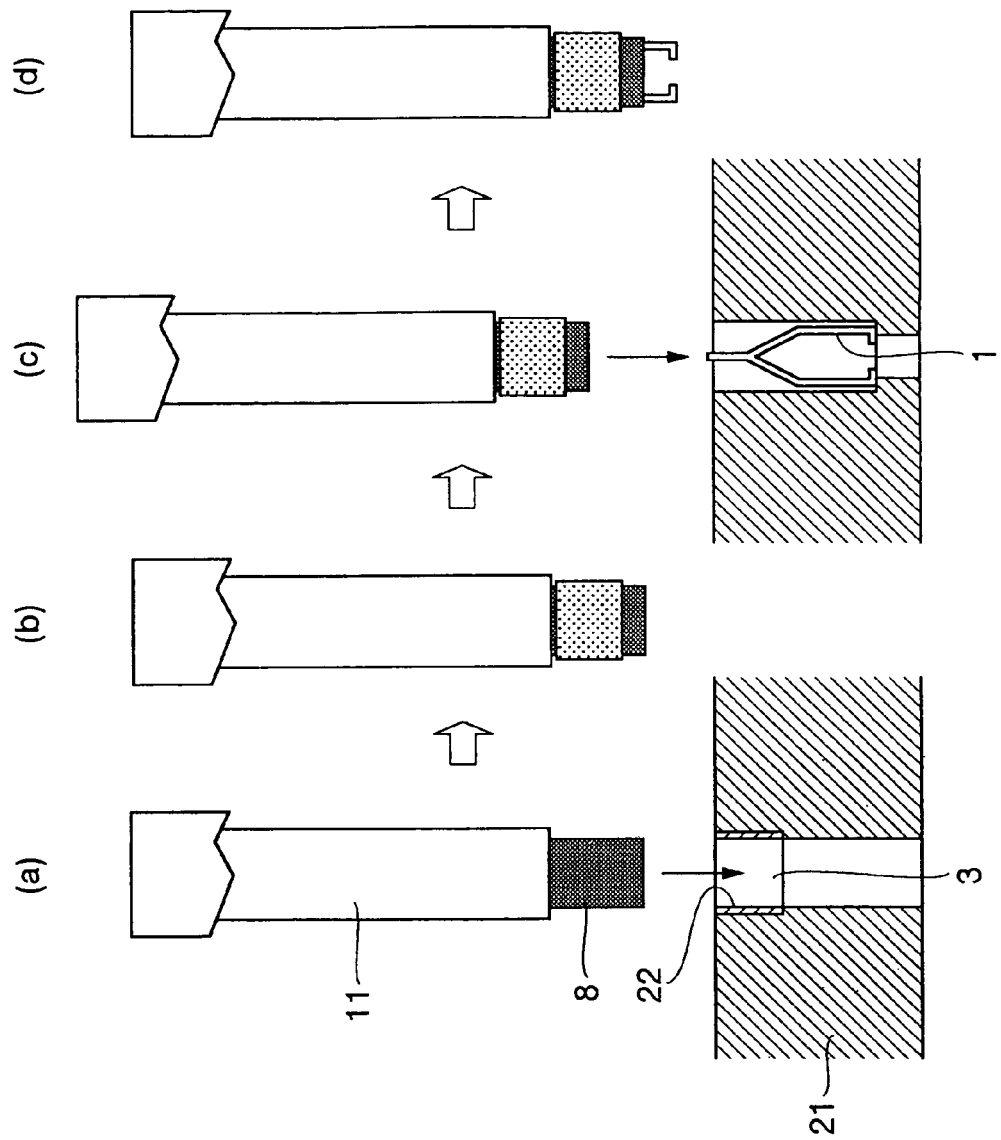
FIGS. 6(a) to 6(d) are views for describing a method of mounting a clip to a clip device for an endoscope.

The sheath 8 is compressed to the fixing means 3 which is previously set to the plate 21 in a state of closing the operating means 2 (FIG. 6(a)), and the fixing means 3 is loaded to the outer periphery of the sheath 8 (FIG. 6(b)). Next, the sheath 8 is compressed to the clip 1 which is previously set to the plate 21, and the arm portions 5 of the clip 1 are slid into the hooks 10 of the operating arms 7 which are received in the sheath 8 (FIG. 6(c)), whereby the loading is completed (FIG. 6(d)).

FIG. 7 shows a state of the clip 1, the operating arms 7 and the hooks 10 when loading is completed. Although an illustration is omitted here, the fixing means is loaded in the outer periphery of the sheath 8. Since a width of the connection portion 6 of the clip 1 is smaller than a width of the arm portion 5, and the structure is made such that the width is continuously reduced from the arm portions 5 toward the connection portion 6 all around a portion or the entire structure of the arm portions 5, it is possible to insert the arm portions 5 to inner sides of the hooks 10 only from a direction of the connection portion 6 of the clip 1 (an arrow in the drawing) so as to fit and fix).

As mentioned above, in accordance with the present invention, it is possible to load the fixing means 3 and the clip 1 only by compressing the sheath 8 to the plate 21. Further, it is not necessary to independently execute the loading of the fixing means 3 and the clip 1, a plurality of steps can be provided in the small hole 22 of the plate 21, and the loading can be completed by one compressing operation.

In this case, a description will be given of a using procedure of the clip device for the endoscope in accordance with the present invention with reference to FIGS. 9(a) to 9(e), and the effect of the present invention is more clarified.

Figure 9:
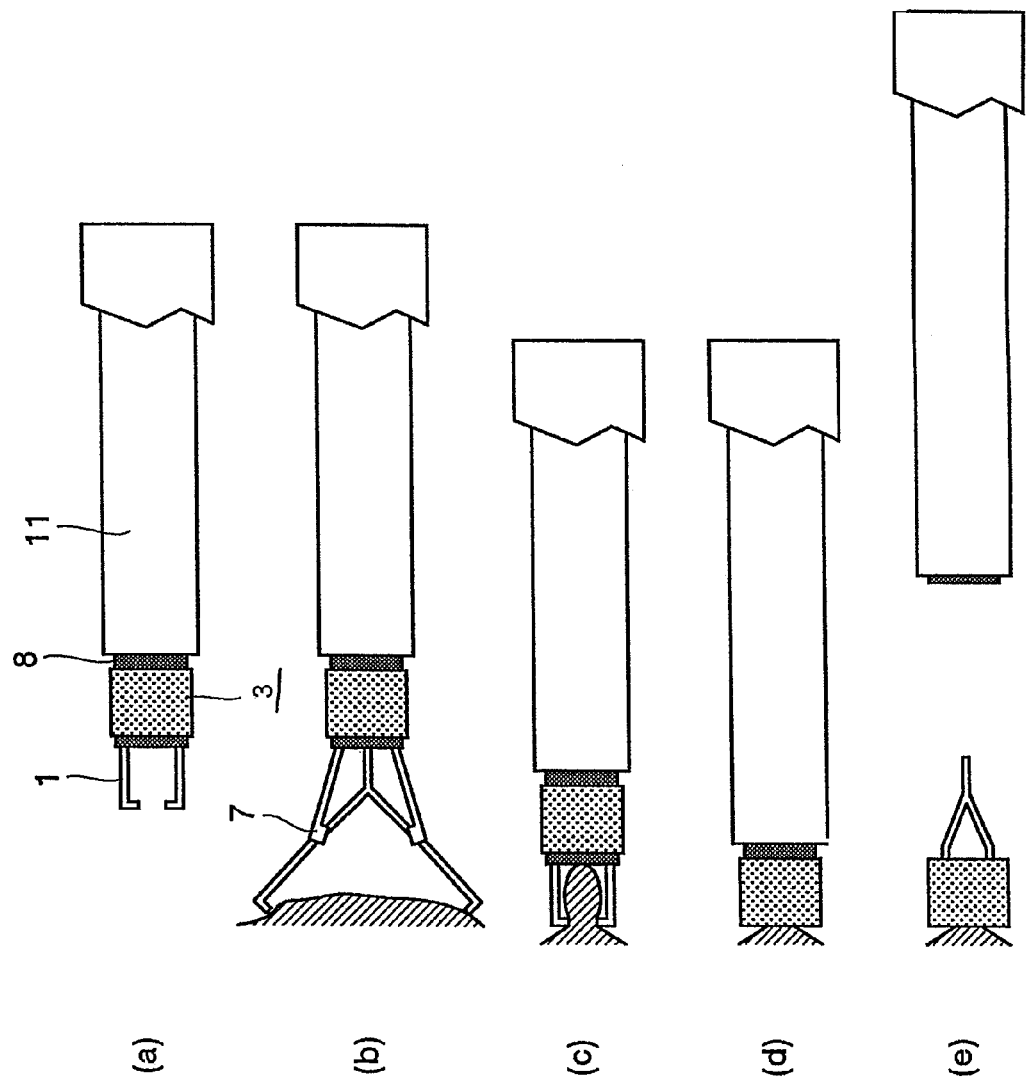
FIGS. 9(a) to 9(d) are views for describing a method of using the clipping device in accordance with the present invention.

After mounting the fixing means 3 on the sheath 8 in a state in which the operating means 2 is closed, the clip 1 is mounted to the operating means 2 (FIG. 9(a)). At this time, the arm portions 5 of the clip 1 are inserted to the inner sides of the hooks 10 provided in the leading ends of the operating arms 7, and the connection portion 6 is inserted to the base portion 9 of the operating means 2.

In the case that the portion to be clipped is defined under the endoscopic operation, the device in accordance with the present invention is introduced. Since the arm portions 5 of the clip 1 are opened by sliding the operating arms 7 to the front side and opening the operating arms 7, the arm portions are pressed against the tissue to be treated in this state. Next, the arm portions 5 are closed by moving the operating arms 7 backward, thereby ligating the tissue (FIGS. 9(b) and 9(c)). At this time, if an effect of the ligature is insufficient, the arm portions 5 are opened by again sliding the operating arms 7 to the front side, whereby it is possible to execute the clipping operation again and again.

In the case that an acceptable clipping is achieved, the arm portions 5 are fastened by sliding the pushing tube 11 to the front side and coating the arm portions 5 with the fixing means 3 (FIG. 9(d)). Thereafter, when the wire 15 and the pushing tube 11 are pulled out together, the clip 1 is released from the operating means 2 and the clipping operation is completed (FIG. 9(e)).

The clip 1 is maintained for some days to one week in a state of ligating the tissue. Thereafter, the tissue becomes necrotic, and the clipping means 1 naturally falls away together with the necrotic portion, and is discharged out of the body.

Figure 10:
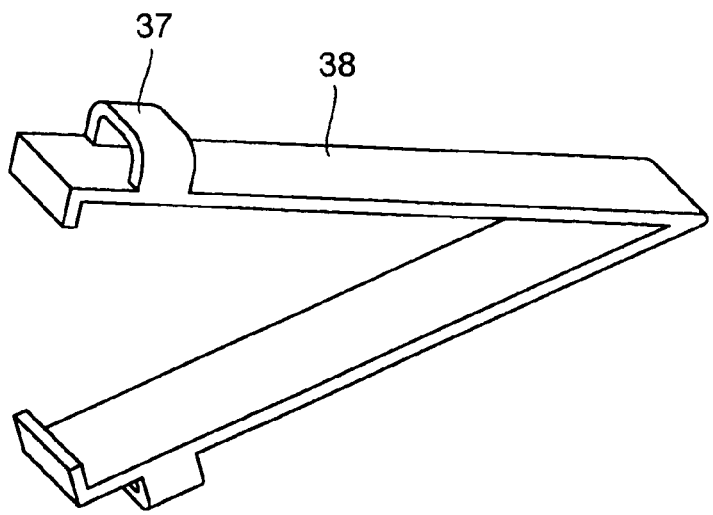
FIG. 10 is a view showing a clip corresponding to a first embodiment in accordance with the present invention.
Figure 11:
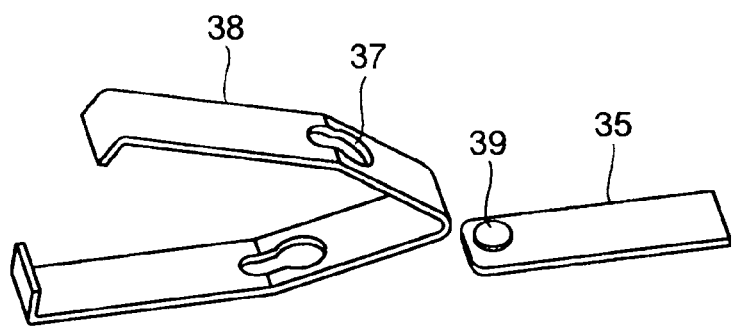
FIG. 11 is a view showing a clip corresponding to a second embodiment in accordance with the present invention.
Figure 12:
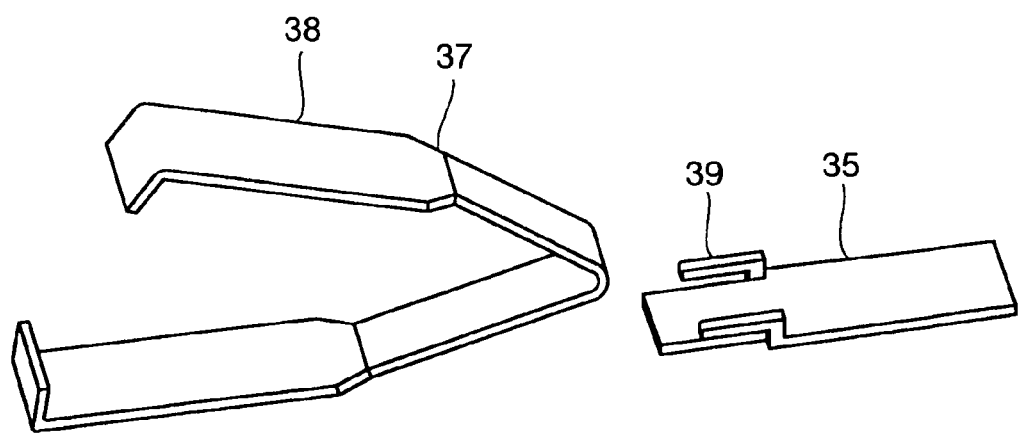
FIG. 12 is a view showing a clip corresponding to a third embodiment in accordance with the present invention.

Next, a description will be given of the clip which is used in the clip device for the endoscope in accordance with an embodiment of the present invention. FIGS. 10, 11 and 12 are views showing a clip in accordance with different embodiments of the present invention. FIG. 13 is a cross sectional view showing a state in which the clip in accordance with the present invention is mounted to the clipping device for the endoscope.

In FIG. 10, a ring-shaped first fixing portion 37 is provided in an arm portion 38 of a clip 31, and the clip 31 can be fixed and opened and closed by passing an operating arm 35 of the clipping device to the first fixing portion 37. A width of the operating arm 35 becomes wide in the middle thereof, and the operating arm 35 is structured such as not to move forward to the first fixing portion 37 at a fixed distance or more.

In FIG. 11, an open first fixing portion 37 is provided in the arm portion 38 of the clip 31, a second fixing portion 39 having a convex-shaped leading end in the operating arm 35 is inserted and fixed to the first fixing portion 37, and the arm 35 is structured such as to be fixed and opened and closed by moving the second fixing portion 39 to a narrower side.

In FIG. 12, the width of the arm portion 38 of the clip 31 is changed in a bent portion, and the first fixing portion 37 is provided by utilizing a width difference. The operating arm 35 is structured such that the second fixing portion 39 is provided and is opened and closed so as to grip the first fixing portion 37.

The first fixing portion 37 and the second fixing portion 39 described in FIGS. 10 to 12 can be fixed and opened and closed even in the case that the clip 31 and the operating arm 35 are inversely mounted.

Further, the clipping device in accordance with the present invention is constituted, as shown in FIG. 13, by a cylindrical tube 33 corresponding to a hollow member having an operating means constituted by a pair of elastic operating arms 35 in a leading end, an operating arm opening and closing tube 32 corresponding to an outer member for covering the cylindrical tube 33 and opening and closing the operating arm 35, a control member 34 connected to the outer member 32, and the clip 31 having an arm portion capable of executing an opening and closing operation.

A description will be given of a principle for executing an opening and closing motion of the present device. The operating arms 35 for fixing and opening and closing the clip 31 are made of a material generating an elastic deformation, and is mounted in a state in which the arms are always open as shown in FIG. 13(b). The arm holding tube 32 is used for making the operating arms 35 in a closed state.

In order to open and close the operating arms 35, it is necessary to move the operating arm opening and closing tube 32 in an axial direction. This motion can be achieved by bonding the control member 34 at a bonding point 36 and moving the control member 34 in the axial direction. The control member 34 passes through an inner portion of the cylindrical tube 33, however, may pass through an outer portion of the cylindrical tube 33. At this time, any shape of the control member 34 can be employed as far as the control member 34 can control the operating arm opening and closing tube 32.

It is possible to carry out the operation of opening and closing the clip 31 without changing the position of the clip 31, by employing the operating principle described above. Further, on the contrary, it is possible to open and close the clip 31 while moving the clip 31 by fixing the control member 34 and moving the cylindrical tube 33.

Next, a description will be given of the first fixing portion 37 to the arms. In accordance with an example of a method of fixing the clip 31 to the operating arms 35, as shown in FIG. 10, the clip can be fixed by applying the ring-shaped first fixing portion 37 to the clip 21 and passing the operating arms 35 therethrough. In FIG. 10, the ring shape is provided in the clip 31 side, however, may be provided in the operating arm 35 side conversely.

Further, in connection with the first fixing portion 37 to the arms, the fixing means 37 is formed in the ring shape in the drawing, however, it is possible to employ any means which can fix the clip 31 to the operating arms 35, such as a fitting utilizing a concavity and convexity, an adhesive agent and the like.

A description will be given of a fixing means of the clip after being clipped.

There can be listed up a method of utilizing a spring elasticity of the clip 31 as one example. This structure is made such that the clip 31 is manufactured in a closed state, the clip 31 is opened by using a force generated by the opening of the operating arms 35 at a time of clipping, and the clip 31 is closed by utilizing a restoring force of the clip 31 after finishing the clipping.

Further, it is possible to employ a method of independently arranging the ring, for fixing the clip 31. There can be listed up a method of fixing the fixing ring to the clip 31 by arranging the ring in the leading end of the operating arm opening and closing tube 32 and protruding the operating arm opening and closing tube 32 from the operating arm 35, a method of arranging the fixing ring in the outer periphery of the operating arm opening and closing tube 32 and extruding the fixing ring by the pushing tube covering the operating arm opening and closing tube 32 and the cylindrical tube 33, and the like.

A description will be given below of an operating procedure of the clipping device using the clip in accordance with the present invention.

The clip 31 is mounted to the first fixing portion 37 in a state in which the opening arm 35 is closed as shown in FIG. 13(a). Next, the present device is introduced after the portion to be clipped is defined under the endoscopic operation. Since the operating arm opening and closing tube 32 is moved to the rear side by moving the control member 34 to the rear side, and the operating arm 35 and the endoscope clip 31 are opened as shown in FIG. 13(b), the operating arm 35 and the endoscope clip 31 are compressed to the tissue to be treated. Next, the control member 34 is moved forward, the operating arm 35 is closed, and the tissue is ligated. At this time, if the ligature is insufficient, the operating arm 35 is opened by moving the control member 34 to the rear side. Accordingly, it is possible to carry out the clipping operation again and again.

In the case that the acceptable clipping is achieved, the clip 31 is fastened by means of the operating arm opening and closing tube 32, by further moving the control member 34 to the front side, and the endoscope clip 31 is fixed by the fixing means (not shown) of the clip. Since the clip 31 is fixed to the tissue, the operating arm 32 comes off from the first fixing portion 37 by moving the entire clipping device to the rear side.

The clip 31 is maintained for some days to one week in a state of ligating the tissue. Thereafter, the tissue becomes necrotic, and the clipping means 1 naturally falls away together with the necrotic portion, and is discharged out of the body.

INDUSTRIAL APPLICABILITY

As is apparent from the above description, since the clipping device for the endoscope in accordance with the present invention can freely open and close the clip, it is possible to carry out the clipping operation again and again and it is possible to easily mount the clip. Accordingly, the clip device for the endoscope in accordance with the present invention is extremely effective for the clip device used in marking for clarifying the area for carrying out the treatment such as the ligature, the resecting and the like of the bleeding portion in the biological tissue under the endoscopic operation.

The invention claimed is:

1. A clip device for an endoscope comprising:
   a hollow member having a pair of operating means in a leading end of said clip device, said operating means being constituted for holding a pair of elastic operating arms so as to open and close said operating arms;
   an outer member covering said hollow member and provided for opening and closing the operating means;
   wherein said elastic operating arms are restored to an open position when said operating arms are slid out from said outer member;
   a control member connected to said outer member;
   a clip having arm portions being capable of being opened and closed by said pair of elastic operating arms; and
   a fixing means arranged on an outer periphery of the outer member for fixing the clip after clipping,
   wherein the operating means is opened and closed by moving the control member connected to the outer member in an axial direction.

2. A clip device for an endoscope as claimed in claim 1, wherein the arm portions of the clip have a means for fixing to the operating arms.

3. A clip device for an endoscope as claimed in claim 1, wherein the operating arms have a means for fixing to the arm portions of the clip.

4. A clip device for an endoscope as claimed in claim 1, wherein the arm portions of the clip means are connected in a base portion in a state in which a width thereof is continuously reduced along a part of or along an entire length of the arm portions.

5. A clip device for an endoscope as claimed in claim 1, wherein the arm portion of the clip is always closed in a clip single body state, on the basis of an elasticity of the clip or another elastic body mounted to the arm portions.

6. A clip device for an endoscope as claimed in claim 1, wherein the fixing means and the clip are previously arranged in a small hole provided on a plate, and are thereafter loaded to the device.

* * * * *